United States Patent
Callens

(10) Patent No.: US 10,912,723 B2
(45) Date of Patent: Feb. 9, 2021

(54) HAIR CONDITIONING COMPOSITION COMPRISING MONOALKYL GLYCERYL ETHER

(71) Applicant: The Procter & Gamble Company, Cincinnati, OH (US)

(72) Inventor: Cedric Kofi Aurelien Callens, Singapore (SG)

(73) Assignee: The Procter and Gamble Company, Cincinnati, OH (US)

( * ) Notice: Subject to any disclaimer, the term of this patent is extended or adjusted under 35 U.S.C. 154(b) by 86 days.

(21) Appl. No.: 15/411,175

(22) Filed: Jan. 20, 2017

(65) Prior Publication Data

US 2017/0202760 A1 Jul. 20, 2017

Related U.S. Application Data

(60) Provisional application No. 62/280,717, filed on Jan. 20, 2016.

(51) Int. Cl.
| | |
|---|---|
| *A61Q 5/00* | (2006.01) |
| *A61K 8/34* | (2006.01) |
| *A61K 8/67* | (2006.01) |
| *A61K 8/42* | (2006.01) |
| *A61K 8/44* | (2006.01) |
| *A61K 8/41* | (2006.01) |
| *A61Q 5/06* | (2006.01) |
| *A61Q 5/12* | (2006.01) |

(52) U.S. Cl.
CPC .............. *A61K 8/345* (2013.01); *A61K 8/342* (2013.01); *A61K 8/416* (2013.01); *A61K 8/42* (2013.01); *A61K 8/44* (2013.01); *A61K 8/675* (2013.01); *A61Q 5/06* (2013.01); *A61Q 5/12* (2013.01); *A61K 2800/262* (2013.01); *A61K 2800/30* (2013.01)

(58) Field of Classification Search
None
See application file for complete search history.

(56) References Cited

U.S. PATENT DOCUMENTS

| | | | |
|---|---|---|---|
| 2,396,278 A | 3/1946 | Lind | |
| 2,438,091 A | 3/1948 | Lynch | |
| 2,486,921 A | 11/1949 | Byerly | |
| 2,486,922 A | 11/1949 | Strain | |
| 2,528,378 A | 10/1950 | Mannheimer | |
| 2,658,072 A | 11/1953 | Kosmin | |
| 2,809,971 A | 10/1957 | Bernstein | |
| 2,826,551 A | 3/1958 | Geen | |
| 3,236,733 A | 2/1966 | Karsten | |
| 3,753,196 A | 8/1973 | Kurtz | |
| 3,761,418 A | 9/1973 | Parran | |
| 3,829,563 A | 8/1974 | Barry et al. | |
| 3,912,665 A | 10/1975 | Spitzer et al. | |
| 3,912,666 A | 10/1975 | Spitzer et al. | |
| 3,929,678 A | 12/1975 | Laughlin | |
| 3,964,500 A | 6/1976 | Drakoff | |
| 4,152,416 A | 5/1979 | Marra | |
| 4,197,865 A | 4/1980 | Jacquet | |
| 4,214,038 A | 7/1980 | McCarty et al. | |
| 4,217,914 A | 8/1980 | Jacquet | |
| 4,275,055 A | 6/1981 | Nachtigal | |
| 4,323,683 A | 4/1982 | Bolich, Jr. | |
| 4,345,080 A | 8/1982 | Bolich, Jr. | |
| 4,364,837 A | 12/1982 | Pader | |
| 4,379,753 A | 4/1983 | Bolich, Jr. | |
| 4,381,919 A | 5/1983 | Jacquet | |
| 4,389,418 A | 6/1983 | Burton | |
| 4,422,853 A | 12/1983 | Jacquet | |
| 4,470,982 A | 9/1984 | Winkler | |
| 4,472,291 A | 9/1984 | Rosano | |
| 4,487,760 A * | 12/1984 | Yamamoto ............. | A61K 8/345 424/47 |
| 4,507,280 A | 3/1985 | Pohl | |
| 4,529,586 A | 7/1985 | De Marco | |
| 4,637,933 A | 1/1987 | Zabotto nee Arribau et al. | |
| 4,663,158 A | 5/1987 | Wolfram | |
| 4,673,526 A | 6/1987 | Zabotto et al. | |
| 4,741,855 A | 5/1988 | Grote | |
| 4,746,460 A | 5/1988 | Taylor | |
| 4,774,016 A | 9/1988 | Gazzani | |
| 4,897,214 A | 1/1990 | Gazzani | |
| 4,954,335 A | 9/1990 | Janchipraponvej | |
| 4,997,641 A | 3/1991 | Hartnett et al. | |
| 5,093,023 A | 3/1992 | Pantini et al. | |

(Continued)

FOREIGN PATENT DOCUMENTS

| | | |
|---|---|---|
| CN | 1579364 A | 2/2005 |
| CN | 1875915 A | 12/2006 |

(Continued)

OTHER PUBLICATIONS

Michael Starch: "New Cosmetic Ingredients Based on Soybean Oil", IP.com Journal, West Henrietta, NY, US, Jun. 15, 2007.
PCT International Search Report and Written Opinion for PCT/US2015/053609 dated Dec. 7, 2015.
Crepaldi, E., et al. Journal Colloid Interfac. Science 2002, Issue 248, pp. 429-442.
Encyclopedia of Polymer Science and Engineering, vol. 15, 2d ed., pp. 204-308, "Silicones" John Wiley & Sons, Inc. (1989).
Morioka, H. et al. "Effects of Zinc on the New Preparation Method of Hydroxy Double Salts" Inorg. Chem. 1999, 38, 4211-6.
"Delivering Solutions, Creating Value", Jun. 25, 2009.
PCT International Search Report and Written Opinion for PCT/US2013/035428; dated Jun. 17, 2014.

(Continued)

*Primary Examiner* — Susan T Tran
(74) *Attorney, Agent, or Firm* — Angela K. Haughey

(57) ABSTRACT

Disclosed is a hair conditioning composition comprising: (a) a cationic surfactant; (b) a high melting point fatty compound having a melting point of 25° C. or higher; (c) a monoalkyl glyceryl ether; and (d) an aqueous carrier. The compositions of the present invention provide styling and/or volume benefits together with conditioning benefits.

4 Claims, No Drawings

(56) References Cited

U.S. PATENT DOCUMENTS

| | | |
|---|---|---|
| 5,104,646 A | 4/1992 | Bolich, Jr. |
| 5,106,609 A | 4/1992 | Bolich, Jr. |
| 5,106,613 A | 4/1992 | Hartnett et al. |
| RE34,584 E | 4/1994 | Grote |
| 5,389,676 A | 2/1995 | Michaels |
| 5,431,913 A | 7/1995 | Phillips |
| 5,466,719 A | 11/1995 | Jakobson et al. |
| 5,587,155 A | 12/1996 | Ochiai et al. |
| 5,624,666 A | 4/1997 | Coffindaffer |
| 5,639,450 A | 6/1997 | Oldenhove De Guertechin |
| 5,674,478 A | 10/1997 | Dodd |
| 5,690,947 A | 11/1997 | Habif |
| 5,710,114 A | 1/1998 | Pyles |
| 5,750,122 A | 5/1998 | Evans |
| 5,776,872 A | 7/1998 | Giret et al. |
| 5,879,584 A | 3/1999 | Bianchetti et al. |
| 5,888,492 A | 3/1999 | Starch |
| 5,942,216 A | 8/1999 | Herb |
| 6,013,682 A | 1/2000 | Dalle |
| 6,117,915 A | 9/2000 | Pereira |
| 6,221,370 B1 | 4/2001 | Wadle et al. |
| 6,303,109 B1 | 10/2001 | Foerster et al. |
| 6,342,208 B1 | 1/2002 | Hyldgaard et al. |
| 6,407,051 B1 | 6/2002 | Smith et al. |
| 6,419,909 B1 | 7/2002 | Lorant et al. |
| 6,420,013 B1 | 7/2002 | Vinson et al. |
| 6,492,315 B1 | 12/2002 | Cao et al. |
| 6,528,070 B1 | 3/2003 | Bratescu et al. |
| 6,534,069 B1 | 3/2003 | Asmus |
| 6,569,414 B1 | 5/2003 | Bernecker et al. |
| 6,602,494 B1 | 8/2003 | Jahedshoar et al. |
| 6,607,733 B1 | 8/2003 | Diec et al. |
| 6,616,917 B2 | 9/2003 | Lorant et al. |
| 6,649,155 B1 | 11/2003 | Dunlop |
| 6,878,773 B2 | 4/2005 | Marteaux et al. |
| 7,267,107 B2 | 9/2007 | Nieendick et al. |
| 7,297,717 B2 | 11/2007 | Iwai et al. |
| 7,476,393 B2 | 1/2009 | Dubief et al. |
| 7,588,797 B2 | 9/2009 | Skoog et al. |
| 7,647,630 B2 | 1/2010 | Arroyo et al. |
| 7,687,066 B2 | 3/2010 | Fujino et al. |
| 7,736,662 B2 | 6/2010 | Amari et al. |
| 7,833,516 B2 | 11/2010 | Fack et al. |
| 7,833,517 B2 | 11/2010 | Fack et al. |
| 7,871,601 B2 | 1/2011 | Watanabe |
| 7,887,857 B1 | 2/2011 | Johnson |
| 7,901,699 B2 | 3/2011 | Takase et al. |
| 7,975,295 B2 | 7/2011 | Arroyo et al. |
| 8,343,470 B2 | 1/2013 | Hloucha et al. |
| 8,372,382 B2 | 2/2013 | Norman |
| 8,454,941 B2 | 6/2013 | Ohrmann et al. |
| 8,501,823 B2 | 8/2013 | Fujino et al. |
| 8,501,973 B2 | 8/2013 | Schrodi et al. |
| 8,518,386 B2 | 8/2013 | Dierker et al. |
| 8,536,356 B2 | 9/2013 | Carvin et al. |
| 8,545,827 B2 | 10/2013 | Molenda et al. |
| 8,603,449 B2 | 12/2013 | Sunkel et al. |
| 8,603,508 B2 | 12/2013 | Norman |
| 8,628,760 B2 | 1/2014 | Carter et al. |
| 8,642,824 B2 | 2/2014 | Lemke et al. |
| 8,658,581 B2 | 2/2014 | Hloucha et al. |
| 8,692,006 B2 | 4/2014 | Uptain et al. |
| 8,715,629 B2 | 5/2014 | Schmid et al. |
| 8,715,631 B2 | 5/2014 | Araujo et al. |
| 8,722,069 B2 | 5/2014 | Amalric et al. |
| 8,748,646 B2 | 6/2014 | Kluesener et al. |
| 8,765,651 B2 | 7/2014 | Hutton, III et al. |
| 8,815,257 B2 | 8/2014 | Braksmayer et al. |
| 8,815,264 B2 | 8/2014 | Wolff et al. |
| 8,821,844 B2 | 9/2014 | Dierker et al. |
| 8,865,193 B2 | 10/2014 | Wolff et al. |
| 8,883,698 B2 | 11/2014 | Scheibel et al. |
| 8,920,786 B2 | 12/2014 | Hloucha et al. |
| 8,933,131 B2 | 1/2015 | Federle et al. |
| 8,936,796 B2 | 1/2015 | Kitko et al. |
| 8,936,798 B2 | 1/2015 | Kitko et al. |
| 8,957,268 B2 | 2/2015 | Cohen et al. |
| 8,961,943 B2 | 2/2015 | Schroder et al. |
| 9,023,330 B2 | 5/2015 | Takiguchi et al. |
| 9,382,189 B2 | 7/2016 | Dubois et al. |
| 9,655,821 B2 | 5/2017 | Carter et al. |
| 9,668,955 B2 | 6/2017 | Braksmayer et al. |
| 9,993,404 B2 | 6/2018 | Callens et al. |
| 10,806,688 B2 | 10/2020 | Stella |
| 2001/0053374 A1 | 12/2001 | Darlrymple et al. |
| 2002/0051797 A1 | 5/2002 | Jezior |
| 2002/0168327 A1 | 11/2002 | Bailey |
| 2003/0083212 A1 | 5/2003 | Willard |
| 2003/0095990 A1 | 5/2003 | Hua et al. |
| 2003/0134771 A1 | 7/2003 | Ellson et al. |
| 2004/0048996 A1 | 3/2004 | Lange |
| 2004/0115155 A1* | 6/2004 | Salvador ............ A61K 8/342 424/70.13 |
| 2004/0138400 A1 | 7/2004 | Lange |
| 2004/0197294 A1 | 10/2004 | Seipel et al. |
| 2004/0223941 A1 | 11/2004 | Schwartz et al. |
| 2004/0234491 A1 | 11/2004 | Brautigam et al. |
| 2004/0258647 A1 | 12/2004 | Ruppert et al. |
| 2005/0031568 A1 | 2/2005 | Deckner |
| 2005/0031653 A1 | 2/2005 | Kwetkat et al. |
| 2005/0031659 A1 | 2/2005 | Deckner |
| 2005/0031660 A1 | 2/2005 | Deckner |
| 2005/0032916 A1 | 2/2005 | Deckner |
| 2005/0053634 A1 | 3/2005 | Ruppert et al. |
| 2005/0112157 A1 | 5/2005 | Ruppert et al. |
| 2005/0186167 A1 | 8/2005 | Ueda |
| 2005/0190942 A1 | 9/2005 | Moquin et al. |
| 2005/0232888 A1* | 10/2005 | Weber ............ A61K 8/891 424/70.12 |
| 2006/0008482 A1 | 1/2006 | Prinz et al. |
| 2006/0013787 A1 | 1/2006 | Sebillotte-Arnaud |
| 2006/0018863 A1 | 1/2006 | Mougin et al. |
| 2006/0024256 A1 | 2/2006 | Wells et al. |
| 2006/0078525 A1 | 4/2006 | Tomokuni |
| 2006/0078528 A1 | 4/2006 | Yang |
| 2006/0096041 A1 | 5/2006 | Molenda |
| 2006/0099167 A1 | 5/2006 | Staudigel |
| 2006/0127344 A1 | 6/2006 | Zofchak |
| 2006/0165739 A1 | 7/2006 | Komesvarakul et al. |
| 2006/0286052 A1 | 12/2006 | Oki et al. |
| 2006/0293213 A1* | 12/2006 | Uehara ............ A61K 8/898 510/466 |
| 2007/0041929 A1 | 2/2007 | Torgerson |
| 2007/0110696 A1 | 5/2007 | Schwartz |
| 2007/0128147 A1 | 6/2007 | Schwartz |
| 2007/0237798 A1 | 10/2007 | Apostol |
| 2007/0248562 A1 | 10/2007 | Berry |
| 2007/0275866 A1 | 11/2007 | Dykstra |
| 2007/0286837 A1 | 12/2007 | Torgerson |
| 2007/0298004 A1 | 12/2007 | Li |
| 2008/0057016 A1 | 3/2008 | Geary et al. |
| 2008/0081023 A1 | 4/2008 | Deckner et al. |
| 2008/0206355 A1 | 8/2008 | Schwartz |
| 2008/0292574 A1 | 11/2008 | Uehara |
| 2008/0292575 A1 | 11/2008 | Uehara |
| 2008/0311068 A1 | 12/2008 | Runglertkriangkrai |
| 2008/0317698 A1 | 12/2008 | Wells |
| 2009/0041704 A1 | 2/2009 | Molenda et al. |
| 2009/0107062 A1 | 4/2009 | Pedersen |
| 2009/0130220 A1 | 5/2009 | Johnson |
| 2009/0143267 A1 | 6/2009 | Zhang |
| 2009/0176675 A1 | 7/2009 | Peffly et al. |
| 2009/0217568 A1 | 9/2009 | Murphy |
| 2009/0220443 A1 | 9/2009 | Braksmayer et al. |
| 2009/0232873 A1 | 9/2009 | Glenn, Jr. |
| 2009/0246236 A1 | 10/2009 | Kitko |
| 2009/0258085 A1 | 10/2009 | Bach |
| 2009/0324527 A1 | 12/2009 | Okada et al. |
| 2009/0324528 A1 | 12/2009 | Okada et al. |
| 2009/0324529 A1 | 12/2009 | Okada et al. |
| 2009/0324531 A1 | 12/2009 | Okada et al. |
| 2009/0324532 A1 | 12/2009 | Okada et al. |
| 2010/0047499 A1 | 2/2010 | Braksmayer et al. |
| 2010/0143282 A1 | 6/2010 | Yokogi |

(56) References Cited

U.S. PATENT DOCUMENTS

| | | | |
|---|---|---|---|
| 2010/0145086 A1 | 6/2010 | Schrodi et al. | |
| 2010/0179083 A1 | 7/2010 | Glenn, Jr. | |
| 2010/0215596 A1 | 8/2010 | Amela Conesa et al. | |
| 2010/0316684 A1 | 12/2010 | Daniels | |
| 2011/0020253 A1 | 1/2011 | Doyle | |
| 2011/0028424 A1 | 2/2011 | Zhang et al. | |
| 2011/0045039 A1 | 2/2011 | Sunkel et al. | |
| 2011/0070173 A1 | 3/2011 | Yoshida et al. | |
| 2011/0113679 A1 | 5/2011 | Cohen et al. | |
| 2011/0135587 A1* | 6/2011 | Kinoshita | A61K 8/342 424/70.11 |
| 2011/0160472 A1 | 6/2011 | Lemke et al. | |
| 2011/0165103 A1 | 7/2011 | Molenda | |
| 2011/0166370 A1 | 7/2011 | Saunders et al. | |
| 2011/0201533 A1 | 8/2011 | Ponder et al. | |
| 2011/0311655 A1 | 12/2011 | Ross | |
| 2012/0010303 A1 | 1/2012 | Mujkic et al. | |
| 2012/0020909 A1 | 1/2012 | Courel et al. | |
| 2012/0171263 A1 | 7/2012 | Capelas Romeu et al. | |
| 2013/0045961 A1 | 2/2013 | Smith, III et al. | |
| 2013/0280174 A1 | 10/2013 | Lipic et al. | |
| 2013/0280192 A1 | 10/2013 | Carter et al. | |
| 2013/0280193 A1 | 10/2013 | Carter et al. | |
| 2013/0280356 A1 | 10/2013 | Stella et al. | |
| 2013/0281551 A1 | 10/2013 | Stella et al. | |
| 2013/0344012 A1 | 12/2013 | Cohen et al. | |
| 2014/0023606 A1 | 1/2014 | Scheunemann et al. | |
| 2014/0302103 A1 | 4/2014 | Carter | |
| 2014/0309154 A1 | 4/2014 | Carter | |
| 2014/0219936 A1 | 8/2014 | Amalric et al. | |
| 2014/0275595 A1 | 9/2014 | Wampler et al. | |
| 2014/0275681 A1 | 9/2014 | Cohen et al. | |
| 2014/0290688 A1 | 10/2014 | Takiguchi et al. | |
| 2014/0357714 A1 | 12/2014 | Braksmayer et al. | |
| 2014/0377205 A1 | 12/2014 | Uehara et al. | |
| 2015/0059995 A1 | 3/2015 | Ramaratnam et al. | |
| 2015/0360015 A1 | 12/2015 | Rabe et al. | |
| 2015/0360016 A1 | 12/2015 | Rabe et al. | |
| 2016/0023989 A1 | 1/2016 | Allen | |
| 2016/0067153 A1 | 3/2016 | Chen et al. | |
| 2016/0090555 A1 | 3/2016 | Frankenbach et al. | |
| 2016/0095807 A1 | 4/2016 | Stella et al. | |
| 2016/0095808 A1 | 4/2016 | Okada et al. | |
| 2016/0095809 A1 | 4/2016 | Stella et al. | |
| 2016/0206532 A1 | 7/2016 | Callens et al. | |
| 2016/0206533 A1 | 7/2016 | Callens et al. | |
| 2016/0244698 A1 | 8/2016 | Schubert et al. | |
| 2016/0244915 A1 | 8/2016 | Mohammadi et al. | |
| 2017/0000711 A1* | 1/2017 | Jansen | A61K 8/19 |
| 2017/0009184 A1 | 1/2017 | Schubert et al. | |
| 2017/0087068 A1 | 3/2017 | Callens et al. | |
| 2017/0174413 A1 | 6/2017 | Callens et al. | |
| 2017/0333314 A1 | 11/2017 | Braksmayer et al. | |
| 2018/0008520 A1 | 1/2018 | Zannoni et al. | |
| 2018/0008843 A1 | 1/2018 | Zannoni et al. | |
| 2018/0009184 A1 | 1/2018 | Mita | |
| 2018/0009402 A1 | 1/2018 | Cha et al. | |
| 2018/0010060 A1 | 1/2018 | Zannoni et al. | |
| 2018/0037848 A1 | 2/2018 | Schubert et al. | |
| 2018/0049969 A1 | 2/2018 | Stella et al. | |
| 2018/0049970 A1 | 2/2018 | Stella et al. | |
| 2018/0051235 A1 | 2/2018 | Schubert et al. | |
| 2018/0092820 A1 | 4/2018 | Stella et al. | |
| 2018/0092825 A1 | 4/2018 | Stella et al. | |
| 2019/0290573 A1 | 9/2019 | Stella | |

FOREIGN PATENT DOCUMENTS

| | | |
|---|---|---|
| CN | 101032451 A | 9/2007 |
| CN | 101664369 A | 3/2010 |
| CN | 102389378 A | 3/2012 |
| CN | 102188331 B | 8/2016 |
| DE | 2130485 A1 | 12/1972 |
| DE | 19732015 C1 | 7/1998 |
| DE | 19710155 A1 | 9/1998 |
| DE | 19851451 A1 | 5/2000 |
| DE | 19903717 A1 | 8/2000 |
| DE | 19907408 A1 | 8/2000 |
| DE | 19943585 A1 | 3/2001 |
| DE | 10237735 A1 | 2/2004 |
| DE | 10239647 A1 | 3/2004 |
| DE | 10239712 A1 | 3/2004 |
| DE | 102004025287 A1 | 12/2005 |
| DE | 102004062771 A1 | 6/2006 |
| DE | 102007028027 A1 | 12/2008 |
| DE | 102011088928 A1 | 8/2012 |
| DE | 102011015192 A1 | 9/2012 |
| EP | 60372 A1 | 9/1982 |
| EP | 0 242 792 A2 | 10/1987 |
| EP | 437956 A1 | 7/1991 |
| EP | 482417 A1 | 4/1992 |
| EP | 0 472 184 B1 | 10/1994 |
| EP | 716848 A1 | 6/1996 |
| EP | 739619 A1 | 10/1996 |
| EP | 1055707 A1 | 11/2000 |
| EP | 1815841 A1 | 8/2007 |
| EP | 2243462 A1 | 10/2010 |
| EP | 2505180 A1 | 10/2012 |
| FR | 2853544 A1 | 10/2004 |
| FR | 2863873 A1 | 6/2005 |
| FR | 2930436 A1 | 10/2009 |
| FR | 2930442 A1 | 10/2009 |
| FR | 2967084 A1 | 5/2012 |
| GB | 1571527 A | 7/1980 |
| GB | 2455294 A | 6/2009 |
| GB | 2485834 A | 5/2012 |
| JP | 55147214 A | 11/1980 |
| JP | 59160532 A | 9/1984 |
| JP | 3284611 A | 4/1994 |
| JP | 6262060 A | 9/1994 |
| JP | 8089786 A | 4/1996 |
| JP | 8259990 A | 10/1996 |
| JP | 9143027 A | 6/1997 |
| JP | 9301835 A | 11/1997 |
| JP | H 107532 | 1/1998 |
| JP | 10036221 A1 | 2/1998 |
| JP | 10139632 A1 | 5/1998 |
| JP | 10180085 A1 | 7/1998 |
| JP | 11043416 A1 | 2/1999 |
| JP | 11090211 A1 | 4/1999 |
| JP | 2000128735 A | 5/2000 |
| JP | 2000189785 A | 7/2000 |
| JP | 2000191454 * | 7/2000 |
| JP | 2000191454 A | 7/2000 |
| JP | 2001011486 A | 1/2001 |
| JP | 2001048744 A | 2/2001 |
| JP | 2001072532 A | 3/2001 |
| JP | 2001181142 A | 7/2001 |
| JP | 2002-053893 A | 2/2002 |
| JP | 2002193740 A | 7/2002 |
| JP | 2002212029 A | 7/2002 |
| JP | 2002338440 A | 11/2002 |
| JP | 2002338499 A | 11/2002 |
| JP | 2003040732 A | 2/2003 |
| JP | 2003055128 A | 2/2003 |
| JP | 2003327506 A | 11/2003 |
| JP | 2004067649 A | 3/2004 |
| JP | 2004238354 A | 8/2004 |
| JP | 2004269502 A | 9/2004 |
| JP | 2004307414 A | 11/2004 |
| JP | 2004359587 A | 12/2004 |
| JP | 4069320 A | 1/2005 |
| JP | 5709304 B2 | 3/2005 |
| JP | 5709304 B2 * | 3/2005 |
| JP | 2005075817 A | 3/2005 |
| JP | 2005132794 A | 5/2005 |
| JP | 2005132806 A | 5/2005 |
| JP | 2005187465 A | 7/2005 |
| JP | 2005239674 A | 9/2005 |
| JP | 2005306872 A | 11/2005 |
| JP | 2005350409 A | 12/2005 |
| JP | 2006160619 A | 6/2006 |
| JP | 2006169198 A | 6/2006 |

(56) References Cited

FOREIGN PATENT DOCUMENTS

| | | |
|---|---|---|
| JP | 2006273752 A | 10/2006 |
| JP | 2006298890 A | 11/2006 |
| JP | 2007153754 A | 6/2007 |
| JP | 2007153806 A | 6/2007 |
| JP | 2007169240 A | 7/2007 |
| JP | 2007191409 A | 8/2007 |
| JP | 2007223938 A | 9/2007 |
| JP | 2007254404 A | 10/2007 |
| JP | 2007254405 A | 10/2007 |
| JP | 2007269722 A | 10/2007 |
| JP | 2007269740 A | 10/2007 |
| JP | 2007277181 A | 10/2007 |
| JP | 2008105952 A | 5/2008 |
| JP | 2008255044 A | 10/2008 |
| JP | 2008297280 A | 12/2008 |
| JP | 2009084238 A | 4/2009 |
| JP | 2009114081 A | 5/2009 |
| JP | 2009126791 A | 6/2009 |
| JP | 2009126843 A | 6/2009 |
| JP | 2009137850 A | 6/2009 |
| JP | 2009137914 A | 6/2009 |
| JP | 2009137915 A | 6/2009 |
| JP | 2009149554 A | 7/2009 |
| JP | 2009161520 A | 7/2009 |
| JP | 2009242269 A | 10/2009 |
| JP | 2009275017 A | 11/2009 |
| JP | 2009292732 A | 12/2009 |
| JP | 2010043027 A | 2/2010 |
| JP | 2010053150 A | 3/2010 |
| JP | 2010195739 A | 9/2010 |
| JP | 2010222317 A | 10/2010 |
| JP | 2010235567 A | 10/2010 |
| JP | 2010248178 A | 11/2010 |
| JP | 2010280643 A | 12/2010 |
| JP | 2010280644 A | 12/2010 |
| JP | 2011001289 A | 1/2011 |
| JP | 2011073976 A | 4/2011 |
| JP | 2011088882 A | 5/2011 |
| JP | 2011126796 A | 6/2011 |
| JP | 2011126797 A | 6/2011 |
| JP | 2011132143 A | 7/2011 |
| JP | 2011144133 A | 7/2011 |
| JP | 2011173843 A | 9/2011 |
| JP | 2011178667 A | 9/2011 |
| JP | 2011190222 A | 9/2011 |
| JP | 2011213681 A | 10/2011 |
| JP | 2011213682 A | 10/2011 |
| JP | 2011246400 A | 12/2011 |
| JP | 2012001597 A | 1/2012 |
| JP | 2012036119 A | 2/2012 |
| JP | 2012077000 A | 4/2012 |
| JP | 2012077001 A | 4/2012 |
| JP | 2012082150 A | 4/2012 |
| JP | 2012082151 A | 4/2012 |
| JP | 4945830 B2 | 6/2012 |
| JP | 2012111723 A | 6/2012 |
| JP | 2012116783 A | 6/2012 |
| JP | 2012131762 A | 7/2012 |
| JP | 2012144466 A | 8/2012 |
| JP | 2012201683 A | 10/2012 |
| JP | 2012206971 A | 10/2012 |
| JP | 2012207000 A | 10/2012 |
| JP | 2012207001 A | 10/2012 |
| JP | 5086019 B2 | 11/2012 |
| JP | 2013227294 A * | 11/2013 |
| JP | 5414064 B2 | 2/2014 |
| KR | 2001036921 A | 5/2001 |
| KR | 2002043422 A | 6/2002 |
| KR | 2008074315 A | 8/2008 |
| KR | 2009073368 A | 7/2009 |
| KR | 2011101411 A | 9/2011 |
| RU | 2020921 C1 | 10/1994 |
| RU | 2025118 C1 | 12/1994 |
| RU | 2026668 C1 | 1/1995 |
| WO | 9112880 A1 | 9/1991 |
| WO | 9406410 A1 | 3/1994 |
| WO | 9505145 A1 | 2/1995 |
| WO | 9614046 A1 | 5/1996 |
| WO | 9723192 A1 | 7/1997 |
| WO | 99/24003 A1 | 5/1999 |
| WO | 2000037166 A | 6/2000 |
| WO | 2000040213 A | 7/2000 |
| WO | 2000064408 A | 11/2000 |
| WO | 2001000143 A | 1/2001 |
| WO | 2001001934 A | 1/2001 |
| WO | WO 01/05358 A1 | 1/2001 |
| WO | 2001006993 A | 2/2001 |
| WO | 2003020237 A | 3/2003 |
| WO | 2003051319 A | 6/2003 |
| WO | 2007051527 A1 | 5/2007 |
| WO | WO2007103398 A1 | 9/2007 |
| WO | 2008007059 A1 | 1/2008 |
| WO | 2008043470 A1 | 4/2008 |
| WO | WO2008091681 A2 | 7/2008 |
| WO | WO2009020665 A1 | 2/2009 |
| WO | WO2009020667 A1 | 2/2009 |
| WO | 2009115428 A1 | 9/2009 |
| WO | WO2010019727 A1 | 2/2010 |
| WO | 2010143802 A1 | 12/2010 |
| WO | 2011/120780 A2 | 10/2011 |
| WO | 2011129784 A2 | 10/2011 |
| WO | 2012002210 A1 | 1/2012 |
| WO | WO2012009525 A2 | 1/2012 |
| WO | 2012130413 A2 | 10/2012 |
| WO | 2012130954 A1 | 10/2012 |
| WO | 2012131624 A1 | 10/2012 |
| WO | WO2014058872 A1 | 4/2014 |
| WO | WO 2014/100970 A1 | 7/2014 |

OTHER PUBLICATIONS

PCT International Search Report and Written Opin for PCT/US2013/035431, dated Jun. 17, 2014.
PCT International Search Report and Written Opinion for PCT/US2014/033018 dated May 30, 2014.
PCT International Search Report and Written Opinion for PCT/US2014/032907 dated Sep. 15, 2014.
Solarek, D.B., "Cationic Starches in Modified Starches: Properties and Uses", Wurzburg, O.B., Ed., CRC Press, Inc., Boca Raton, FL 1986, pp. 113-125.
USPTO Office Actions for U.S. Appl. No. 13/857,522.
USPTO Office Actions for U.S. Appl. No. 13/857,540.
PCT International Search Report and Written Opinion for PCT/US2017/013712 dated May 19, 2017.
PCT International Search Report and Written Opinion for PCT/US2016/013573 dated Apr. 19, 2016.
PCT International Search Report and Written Opinion for PCT/US2016/013571 dated Apr. 1, 2016.
PCT International Search Report and Written Opinion for PCT/US2015/053608 dated Dec. 1, 2015.
PCT International Search Report and Written Opinion for PCT/US2015/053451 dated Dec. 16, 2015.
Mintel, Aug. 2011, "Luxury Moisture Conditioner".
"Composition for protecting hair damaged by e.g. bleaching and permanent wave treatment, contains amidoamine type tertiary cationic surfactant obtained by reacting amidoamine and acid, and mono-alkyl or mono-alkenyl glyceryl ether", Thompson Scientific, London, GB, 2009.
"Glycerol effects on the formation and rheology of hexagonal phase and related gel emulsion", Mohammad Mydul Alam et al., J. Col. Interf. Sci. 336 (2009), pp. 820-826.
Swelling of $L_\alpha$-Phases by Matching the Refractive Index of the Water-Glycerol Mixed Solvent and that of the Bilayers in the Block Copolymer System of $(EO)_{15}$-$(PDMS)_{15}$-$(EO)_{15}$, Yun Yan et al, J. Phys. Chem. B111 (2007) pp. 6374-6382.
All Office Actions, U.S. Appl. No. 14/995,431.
All Office Actions, U.S. Appl. No. 14/995,446.
"DPG-Industrial", Data Sheet, Shell Chemicals, Issued Oct. 23, 2009.

(56) References Cited

OTHER PUBLICATIONS

"Benzyl Alcohol" from Wikipedia, last modified Feb. 2, 2016, printed Mar. 15, 2016.
"Tallow Amines" Chemicalland21.com, printed Mar. 16, 2016.
"Myristic acid" from Wikipedia, last modified Dec. 3, 2015, printed Mar. 15, 2016.
Polyquaternium-10, https://pubchem.ncbi.nlm.nih.gov/compound/71307057#section=Top. Published Mar. 19, 2015.
Hydetaka Akatsuka et al., "Effect of polyols on the shear-induced structure and rheological properties of behenyl trimethyl ammonium chloride/1-octadecano/water ternary systems", Colloids and Surfaces A: Physiochem. Eng. Aspects 326 (2008, 169-174.
All final and non-final office actions for U.S. Appl. No. 13/857,522.
All final and non-final office actions for U.S. Appl. No. 13/857,540.
All final and non-final office actions for U.S. Appl. No. 14/245,254.
All final and non-final office actions for U.S. Appl. No. 14/245,576.
All final and non-final office actions for U.S. Appl. No. 14/506,209.
All final and non-final office actions for U.S. Appl. No. 14/506,229.
All final and non-final office actions for U.S. Appl. No. 14/873,654.
All final and non-final office actions for U.S. Appl. No. 15/044,312.
All final and non-final office actions for U.S. Appl. No. 15/240,259.
All final and non-final office actions for U.S. Appl. No. 15/411,175.
All final and non-final office actions for U.S. Appl. No. 15/655,038.
All final and non-final office actions for U.S. Appl. No. 15/655,075.
All final and non-final office actions for U.S. Appl. No. 15/698,868.
All final and non-final office actions for U.S. Appl. No. 15/700,432.
All final and non-final office actions for U.S. Appl. No. 16/441,929.
Iodine Value—Wikipedia—downloaded Jun. 9, 2008 (5 pages).
PCT International Search Report and Written Opinion for PCT/US2016/018372; dated Jun. 7, 2016.
PCT International Search Report and Written Opinion for PCT/US2016/018376 dated May 2, 2016.
PCT International Search Report and Written Opinion for PCT/US2016/041221 dated Sep. 29, 2016.
PCT International Search Report and Written Opinion for PCT/US2016/047555 dated Apr. 25, 2017.
PCT International Search Report and Written Opinion for PCT/US2017/013712 dated Jul. 12, 2017.
PCT International Search Report and Written Opinion for PCT/US2017/045677 dated Oct. 20, 2017.
PCT International Search Report and Written Opinion for PCT/US2017/0505825 dated Oct. 25, 2017.
PCT International Search Report and Written Opinion for PCT/US2017/050889 dated Oct. 27, 2017.
Schrock, Richard R., et al.; Molybdenum and Tungsten Imido Alkylidene Complexes as Efficient Olefin-Metathesis Catalysts; Angewandte Chemie Int. Ed.; 2003; pp. 4592-4633; vol. 42.
Schrock, Richard R.; High Oxidation State Multiple Metal-Carbon Bonds; Chemical Reviews; 2002; pp. 145-179; vol. 102; No. 1.
Schrock, Richard R.; Recent Advances in High Oxidation State Mo and W Imido Alkylidene Chemistry; Chemical Reviews; 2009; pp. 3211-3226; vol. 109; No. 8.
Univar: Dow Corning® HY-3050 Soy Wax, 3 pages (Apr. 10, 2008).

* cited by examiner

HAIR CONDITIONING COMPOSITION COMPRISING MONOALKYL GLYCERYL ETHER

FIELD OF THE INVENTION

The present invention relates to a hair conditioning composition comprising: (a) a cationic surfactant; (b) a high melting point fatty compound having a melting point of 25° C. or higher; (c) a monoalkyl glyceryl ether; and (d) an aqueous carrier. The compositions of the present invention provides: styling and/or volume benefits together with conditioning benefit.

BACKGROUND OF THE INVENTION

A variety of approaches have been developed to condition the hair. A common method of providing conditioning benefit is through the use of conditioning agents such as cationic surfactants and polymers, high melting point fatty compounds, low melting point oils, silicone compounds, and mixtures thereof. Most of these conditioning agents are known to provide various conditioning benefits. Furthermore, a variety of approaches have been developed to provide other benefits in addition to such conditioning benefits. For example, some conditioning compositions provide styling benefit and/or volume benefit in addition to conditioning benefits.

For example, US patent application publication No. 2014/0290688 from Kao relates to a hair treatment composition comprising: (A) polyglycerin; (B) alkyl glyceryl ester or alkyl glyceryl ether; (C) aromatic alcohol; and (D) cationic surfactant. The US publication discloses in the paragraph [0001] that the present invention relates to a hair treatment composition, which reforms the inside of hair and improves hair styling properties. The US publication also discloses in TABLE 3 in EXAMPLES, such compositions further containing 6.0% of stearyl alcohol, and isostearyl glyceryl ether or 2-ethylhexyl glyceryl ether as the above component (B).

The US publication further discloses in the paragraph [0027] that alkyl glyceryl ester or alkyl glyceryl ether as component (B) creates an emulsified state with a cationic surfactant as component (D) to suppress inhibition of hair styling properties provided to the component (A).

However, there remains a need for conditioning compositions to provide at least one of the following:
improved volume benefit together with conditioning benefits;
styling and/or volume benefits by a different approach together with conditioning benefits; and/or
both conditioning benefits and styling and/or volume benefits, together with translucent product appearance.

Such styling benefits can be ease of styling, hair manageability and/or long lasting style. Such volume benefits can be volume at both top and side and/or long lasting volume. Such styling and/or volume benefits often contradict conditioning benefits, and thus are often compromised in hair conditioning compositions.

None of the existing art provides all of the advantages and benefits of the present invention.

SUMMARY OF THE INVENTION

The present invention is directed to a hair conditioning composition comprising:

(a) a cationic surfactant;
(b) a high melting point fatty compound having a melting point of 25° C. or higher;
(c) a monoalkyl glyceryl ether; and
(d) an aqueous carrier.
wherein the composition is used for providing volume benefits to hair.

The composition of the present invention provides improved volume benefit together with conditioning benefits.

The present invention is also directed to a hair conditioning composition comprising:

(a) a cationic surfactant;
(b) a high melting point fatty compound having a melting point of 25° C. or higher;
(c) a monoalkyl glyceryl ether;
(d) an aqueous carrier;
wherein the composition further comprises a polyol having at least 3 hydroxyl groups, and wherein the composition is a translucent hair conditioning composition having a transmittance of at least about 0.5%.

The composition of the present invention provides both conditioning benefits and styling and/or volume benefits, together with translucent product appearance.

The present invention is further directed to a hair conditioning composition comprising:

(a) a cationic surfactant;
(b) a high melting point fatty compound having a melting point of 25° C. or higher;
(c) a monoalkyl glyceryl ether;
(d) an aqueous carrier;
wherein the composition further comprises niacinamide.

The composition of the present invention provides styling and/or volume benefits together with conditioning benefits.

Such styling benefits can be ease of styling, hair manageability and/or long lasting style. Such volume benefits can be volume at both top and side and/or long lasting volume. Such styling and/or volume benefits often contradict conditioning benefits, and thus are often compromised in hair conditioning compositions. The compositions of the present invention meet contradictional needs which are often compromised in hair conditioning products, i.e., proving styling and/or volume benefits, while providing conditioning benefits These and other features, aspects, and advantages of the present invention will become better understood from a reading of the following description, and appended claims.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

Hair Conditioning Composition

The composition of the present invention comprises: (a) a cationic surfactant; (b) a high melting point fatty compound having a melting point of 25° C. or higher; (c) a monoalkyl glyceryl ether; and (d) an aqueous carrier.

The composition of the present invention further has at least one of the following three elements:
the composition is used for providing volume benefits to hair;
the composition further comprises a polyol having at least 3 hydroxyl groups, which is preferably glycerin, sorbitol, and/or xylitol, and more preferably glycerin, and is a translucent hair conditioning composition having a transmittance of at least about 0.5%; and the composition further comprises a niacinamide.

Preferably, in the composition of the present invention especially when the composition is a translucent composition, it is preferred that the composition is substantially free of polyglycerin.

In the present invention, "the composition being substantially free of polyglycerin" means that: the composition is free of polyglycerins; or, if the composition contains polyglycerins, the level of such polyglycerins is very low. In the present invention, a level of such polyglycerins is, if included, preferably 0.1% or less, more preferably 0.05% or less, still more preferably 0.01% or less by weight of the composition. Most preferably, the level of such polyglycerins is 0% by weight of the composition.

Monoalkyl Glyceryl Ether

The composition of the present invention comprises a monoalkyl glyceryl ether. The monoalkyl glyceryl ether can be included in the composition at a level of preferably from about 0.1%, more preferably from about 0.2%, still more preferably from about 0.5% by weight of the composition, and preferably to about 3%, more preferably to about 2%, still more preferably to about 1% by weight of the composition, in view of providing the benefits of the present invention.

The monoalkyl glyceryl ether is a monoether of glycerin. In the present invention, it is preferred that the monoalkyl portion of the monoalkyl glyceryl ether has from about 6 to about 30 carbons, more preferably from about 12 to about 22 carbons, still more preferably from about 16 to 22 carbons. It also preferred that the monoalkyl portion of the monoalkyl glyceryl ether is a non-branched linear alkyl.

Highly preferred monoalkyl glyceryl ether herein is 1-monostearyl glyceryl ether, which is also known as batyl alcohol.

Niacinamide

In one embodiment, the composition preferably comprises niacinamide. It is believed that by combining niacinamide with the monoalkyl glyceryl ether, the composition provides increased interfiber friction while providing wet and dry smoothness. Thus, it is believed that this combination provides improved styling and/or volume benefits while keeping conditioning benefits.

It is known in the art that increased interfiber friction is a key factor to help providing styling and/or volume benefits, however, conventional ways to provide increased interfiber friction such as addition of particulates and/or styling polymers often deteriorate conditioning benefits such as wet and/or dry smoothness. The combination of niacinamide and monoalkyl glyceryl ethers especially batyl alcohol can provide improved wet smoothness, increased interfiber friction while providing wet and dry smoothness.

The niacinamide can be included in the composition at a level of preferably from about 0.2%, more preferably from about 0.5%, still more preferably from about 1% by weight of the composition in view of providing improved wet conditioning benefit especially wet smoothness upon rinsing and/or dry smoothness, and preferably to about 4%, more preferably to about 3%, still more preferably to about 2% by weight of the composition.

Cationic Surfactant

The compositions of the present invention comprise a cationic surfactant.

In opaque compositions, the cationic surfactant can be included in the composition at a level by weight of preferably from about 0.3% to about 10%, more preferably from about 0.5% to about 8%, still more preferably from about 0.8% to about 5%, even more preferably from about 1.0% to about 4%.

In translucent compositions, the cationic surfactant can be included in the composition at a level of preferably from about 0.3%, more preferably from about 0.5%, still more preferably from about 0.7% by weight of the composition and preferably to about 5%, more preferably to about 3%, still more preferably to about 2% by weight of the composition, in view of balance between providing translucent product appearance and providing conditioning benefits Cationic surfactant useful herein can be one cationic surfactant or a mixture of two or more cationic surfactants. Preferably, the cationic surfactant is selected from: mono-long alkyl quaternized ammonium salt; a combination of mono-long alkyl quaternized ammonium salt and di-long alkyl quaternized ammonium salt; mono-long alkyl amine; a combination of mono-long alkyl amine and di-long alkyl quaternized ammonium salt.

In translucent compositions, among the above cationic surfactants, cationic surfactants being mono-long alkyl amines, more specifically, mono-long alkyl amidoamines are preferred in view of providing translucent product appearance and conditioning benefits.

Mono-long alkyl amine

Mono-long alkyl amine useful herein are those having one long alkyl chain of preferably from 12 to 30 carbon atoms, more preferably from 16 to 24 carbon atoms, still more preferably from 18 to 22 alkyl group. Mono-long alkyl amines useful herein also include mono-long alkyl amidoamines Primary, secondary, and tertiary fatty amines are useful.

Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethyl amine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al.

These amines are used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; more preferably l-glutamic acid, lactic acid, citric acid, at a molar ratio of the amine to the acid of from about 1:0.3 to about 1:2, more preferably from about 1:0.4 to about 1:1.

Mono-long alkyl Quaternized Ammonium Salt

The mono-long alkyl quaternized ammonium salts useful herein are those having one long alkyl chain which has from 12 to 30 carbon atoms, preferably from 16 to 24 carbon atoms, more preferably C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

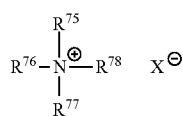

(I)

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and X⁻ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Di-long alkyl Quaternized Ammonium Salts

When used, di-long alkyl quaternized ammonium salts are preferably combined with a mono-long alkyl quaternized ammonium salt or mono-long alkyl amine salt, at the weight ratio of from 1:1 to 1:5, more preferably from 1:1.2 to 1:5, still more preferably from 1:1.5 to 1:4, in view of stability in rheology and conditioning benefits.

Di-long alkyl quaternized ammonium salts useful herein are those having two long alkyl chains of from 12 to 30 carbon atoms, more preferably from 16 to 24 carbon atoms, still more preferably from 18 to 22 carbon atoms. Such di-long alkyl quaternized ammonium salts useful herein are those having the formula (I):

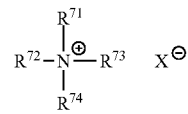

(I)

wherein two of $R^{71}$, $R^{72}$, $R^{73}$ and $R^{74}$ are selected from an aliphatic group of from 12 to 30 carbon atoms, preferably from 16 to 24 carbon atoms, more preferably from 18 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, preferably from 1 to 3 carbon atoms or an aromatic, alkoxy, polyoxyalkylene, alkylamido, hydroxyalkyl, aryl or alkylaryl group having up to about 8 carbon atoms; and X⁻ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Preferably, two of $R^{71}$, $R^{72}$, $R^{73}$ and $R^{74}$ are selected from an alkyl group of from 12 to 30 carbon atoms, preferably from 16 to 24 carbon atoms, more preferably from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Such preferred di-long alkyl cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

High Melting Point Fatty Compound

The compositions of the present invention comprise the high melting point fatty compound. By the use of high melting point fatty compound, the composition of the present invention provides improved conditioning benefits such as friction reduction during conditioner application, ease of spreading, and/or ease of detangling, compared to compositions containing no high melting point fatty compounds and/or compared to compositions containing low melting point fatty compounds instead of high melting point fatty compounds. By the use of high melting point fatty compound, the composition of the present invention may provide improved stability of the composition such as reduced the risk of phase separation, compared to compositions containing no high melting point fatty compounds and/or compared to compositions containing low melting point fatty compounds instead of high melting point fatty compounds.

In opaque compositions, the high melting point fatty compound can be included in the composition at a level of preferably from about 1% to about 20%, more preferably from about 1% to about 15%, still more preferably from about 1.5% to about 10%, even more preferably from about 2% to about 8% by weight of the composition, in view of providing improved conditioning benefits such as slippery feel during the application to wet hair, softness and moisturized feel on dry hair.

In translucent compositions, the high melting point fatty compound can be included in the composition at a level of preferably from about 1.0%, more preferably from about 1.5%, still more preferably from about 2.0%, even more preferably from about 2.5% by weight of the composition in view of providing conditioning benefits, and preferably to about 10%, more preferably to about 8.0%, still more preferably to about 5.0%, even more preferably to about 4.5% by weight of the composition, in view of providing translucent product appearance.

The high melting point fatty compound useful herein have a melting point of 25° C. or higher, preferably 40° C. or higher, more preferably 45° C. or higher, still more preferably 50° C. or higher, in view of stability of the emulsion especially the gel matrix. Preferably, such melting point is up to about 90° C., more preferably up to about 80° C., still more preferably up to about 70° C., even more preferably up to about 65° C., in view of easier manufacturing and easier emulsification. In the present invention, the high melting point fatty compound can be used as a single compound or as a blend or mixture of at least two high melting point fatty compounds. When used as such blend or mixture, the above melting point means the melting point of the blend or mixture.

The high melting point fatty compound useful herein is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than the above preferred in the present invention. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are preferably used in the composition of the present invention. The fatty alcohols useful herein are those having from about 14 to about 30 carbon atoms, preferably from about 16 to about 22 carbon atoms. These fatty alcohols are saturated and can be straight or branched chain alcohols.

Preferred fatty alcohols include, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group.

In the present invention, more preferred fatty alcohol is a mixture of cetyl alcohol and stearyl alcohol.

Generally, in the mixture, the weight ratio of cetyl alcohol to stearyl alcohol is preferably from about 1:9 to 9:1, more preferably from about 1:4 to about 4:1, still more preferably from about 1:2.3 to about 1.5:1

Aqueous Carrier

The composition of the present invention preferably comprises an aqueous carrier. The level and species of the carrier are selected according to the compatibility with other components, and other desired characteristic of the product.

The carrier useful in the present invention includes water and water solutions of lower alkyl alcohols. The lower alkyl alcohols useful herein are monohydric alcohols having 1 to 6 carbons, more preferably ethanol and isopropanol.

Preferably, the aqueous carrier is substantially water. Deionized water is preferably used. Water from natural sources including mineral cations can also be used, depending on the desired characteristic of the product. Generally, the compositions of the present invention comprise from about 20% to about 80%, preferably from about 20% to about 70%, and more preferably from about 30% to about 60%, and more preferably from about 35% to about 55% water by weight of the composition.

Gel Matrix

Preferably, in the present invention, the cationic surfactant, the high melting point fatty compound, and an aqueous carrier form a gel matrix. When polyols are contained in the compositions especially in translucent compositions, the above ingredients preferably form a gel matrix together with polyol. The gel matrix is suitable for providing various conditioning benefits, such as slippery feel during the application to wet hair and softness and moisturized feel on dry hair.

Preferably, when the gel matrix is formed, the cationic surfactant and the high melting point fatty compound are contained at a level such that the weight ratio of the cationic surfactant to the high melting point fatty compound is in the range of, preferably from about 1:1 to about 1:7, more preferably from about 1:1.15 to about 1:5, still more preferably from about 1:2 to about 1:4, in view of providing conditioning benefits and/or translucent product appearance. In this weight ratio, the cationic surfactant is a component without counter ion or acid, for example, when the cationic surfactant is the combination of a mono-long alkyl amine and an acid, the weight of mono-long alkyl amine without the weight of acid is considered in this weight ratio.

Preferably, when the gel matrix is formed, the composition of the present invention is substantially free of anionic surfactants in view of stability of the gel matrix.

In the present invention, "the composition being substantially free of anionic surfactants" means that: the composition is free of anionic surfactants; or, if the composition contains anionic surfactants, the level of such anionic surfactants is very low. In the present invention, a total level of such anionic surfactants, if included, preferably 0.1% or less, more preferably 0.05% or less, still more preferably 0.01% or less by weight of the composition. Most preferably, the total level of such anionic surfactants is 0% by weight of the composition.

Translucent Hair Conditioning Composition

One preferred embodiment of the present invention can be a translucent hair conditioning composition further comprising a polyol having at least 3 hydroxy groups.

In such translucent compositions, the cationic surfactant, the high melting point fatty compound, the polyol, and the aqueous carrier are in the form of emulsion.

In such translucent composition, a total amount of cationic surfactants and high melting point fatty compounds is preferably from about 1.5% to about 10%, more preferably from about 2.0% to about 8.0%, still more preferably from about 2.5% to about 6.0%, in view of providing a balance between conditioning benefits and translucent product appearance.

Transmittance Such translucent composition has a transmittance of at least about 0.5% at 25° C., preferably at least about 1.0%, more preferably at least about 1.5% and preferably up to about 40%, more preferably up to about 30%, still more preferably up to about 20%. This transmittance is for the composition, i.e., final product formulation which can contain additional ingredients such as silicone, perfume and/or preservatives.

The transmittance for the composition base before containing such additional ingredients can be higher. The composition base, thus, consist only of the cationic surfactant, the high melting point fatty compound, the material having a higher refractive index such as polyol, and the aqueous carrier. The composition base has a transmittance of preferably at least about 5% at 25° C., more preferably at least about 7%, still more preferably at least about 10% and preferably up to about 40%, more preferably up to about 30%, still more preferably up to about 25%.

The transmittance in the present invention is a total transmittance which is a sum of diffuse and regular transmission, and which is measured at 600 nm using a Dual-beam spectrophotometer UltraScan Vis, which is a UV visible spectrophotometer available from HunterLab.

Shear Stress

Preferably, in view of spreadability, such translucent composition has a shear stress of at least about 100 Pa, more preferably at least about 120 Pa, still more preferably at least about 140 Pa, and preferably up to about 1000 Pa, more preferably up to about 800 Pa, still more preferably up to about 600 Pa, even more preferably up to about 400 Pa. When the shear stress is too low, the composition is too runny to spread on hair, and drip off from hair and/or hands. When the shear stress is too high, the composition is too hard to spread on hair. This shear stress is for the composition, i.e., final product formulation which can contain additional ingredients such as silicone, perfume and/or preservatives.

The shear stress for the composition base before containing such additional ingredients can be higher. The composition base, thus, consist only of the cationic surfactant, the high melting point fatty compound, the material having a higher refractive index such as polyol, and the aqueous carrier. The composition base has a shear stress of preferably at least about 200 Pa, more preferably at least about 250 Pa, still more preferably at least about 300 Pa, even more preferably at least about 350 Pa, and preferably up to about 1000 Pa, more preferably up to about 800 Pa, still more preferably up to about 600 Pa, even more preferably up to about 400 Pa.

Shear stress is measured by shear rate sweep condition with a rheometer available from TA Instruments with a mode name of ARG2. Geometry has 40 mm diameter, 2° C. cone angle, and gap of 49 μη. Shear rate is logarithmically increased from 0 to 1200/s for 1 min, and temperature is kept at 26.7° C. Share stress at a high shear rate of 950/s is measured and defined above.

Substantially Free of Low Melting Point Fatty Compound

Preferably, such translucent compositions are substantially free of low melting point fatty compounds, in view of stability of the composition such as reduced the risk of phase separation, in view of spreadability by having a preferred shear stress, and/or in view of translucent product appearance.

In the present invention, the compositions being "substantially free" of low melting point fatty compounds means that: the composition is free of low melting point fatty compounds; or, if the composition contains low melting point fatty compound, the level of such low melting point fatty compound is very low. In the present invention, the level of such low melting point fatty compound is, if included, 0.1% or less, preferably 0.05% or less, more preferably 0.01% or less, most preferably 0%.

The low melting point fatty compound herein have a melting point of below 25° C. (not including 25° C.), preferably below 40° C. (not including 40° C.), more preferably below 45° C. (not including 45° C.).

Such low melting point fatty compounds herein include, for example, oleyl alcohol, lauryl alcohol, isopropyl isostearate, isostearyl alcohol, 2-hexyl-1-decanol, caprylic alcohol, decyl alcohol.

Substantially Free of Non-Silicone Thickening Polymers

Preferably, such translucent compositions are substantially free of non-silicone thickening polymers, in view of wet conditioning. Non-silicone thickening polymers herein are polymeric compounds other than silicone polymers, and selected from the group consisting of non-silicone nonionic thickening polymers, non-silicone cationic thickening polymers, non-silicone anionic crosslinked thickening polymers, and mixtures thereof. Non-silicone thickening polymers herein have a molecular weight of at least about 1,000.

In the present invention, the compositions being "substantially free" of non-silicone thickening polymers means that: the composition is free of non-silicone thickening polymers; or, if the composition contains non-silicone thickening polymers, the level of such non-silicone thickening polymers is very low. In the present invention, the level of such non-silicone thickening polymers is, if included, 0.1% or less, preferably 0.05% or less, more preferably 0.01% or less, most preferably 0%.

Non-silicone nonionic thickening polymers include, for example, polysaccharide polymers such as hydroxyethyl cellulose, hydroxypropyl cellulose, guars which are often used as viscosity modifiers/rheology builders. Non-silicone cationic thickening polymers include, for example, cationic celluloses such as polyquaternium-4, polyquaternium-10, cationic guars, and other non-polysaccharide cationic polymers. Non-silicone anionic crosslinked thickening polymers include, for example, carbomer, and Acrylates/C10-30 Alkyl Acrylate Crosspolymer.

Polyols Having at Least Three Hydroxy Groups

In such translucent composition, polyols having at least 3 hydroxy groups are preferably used, which contributes to providing translucent product appearance.

In preferred embodiment, polyols can be included in the composition at a level of above 30% (not including 30%), more preferably from about 40%, still more preferably from about 45%, and preferably to about 80%, more preferably to about 70%, more preferably to about 65% by weight of the composition, in view of providing translucent appearance and having preferred shear stress. It is also preferred to have a certain weight ratio between polyol and a total weight of cationic surfactants and high melting point fatty compounds in view of providing translucent appearance. The weight ratio of polyols to the combination of cationic surfactants and high melting point fatty compounds is preferably from about 6:1 to about 18:1, more preferably from about 8:1 to about 15:1, still more preferably from about 9:1 to about 13:1.

Polyol useful herein are those having a molecular weight of preferably from about 60 to about 500, more preferably from about 60 to about 350, still more preferably from about 60 to about 200, even more preferably from about 60 to about 150.

Preferably, polyols useful herein have at least 3 hydroxyl groups, and preferably up to 12 hydroxyls groups, more preferably up to 10 hydroxyls groups, still more preferably up to 6 hydroxyls groups, even more preferably up to 4 hydroxyls groups.

Polyols useful herein are preferably water soluble. Water soluble polyols herein means those being soluble at a level used at 30° C. Preferably, polyols herein are free of ester bond and ether bond.

Highly preferred herein are glycerin, sorbitol, and xylitol, in view of providing translucent appearance and preferred shear stress. Further preferred are glycerin, in view of translucent appearance and preferred shear stress.

Silicone Compound

The compositions of the present invention may contain a silicone compound. The silicone compounds are included at levels by weight of the composition of from about 0.05% to about 15%, preferably from about 0.1% to about 10%, more preferably from about 0.1% to about 8%.

Preferably, the silicone compounds have an average particle size of from about 1 microns to about 50 microns, in the composition.

The silicone compounds useful herein, as a single compound, as a blend or mixture of at least two silicone compounds, or as a blend or mixture of at least one silicone compound and at least one solvent, have a viscosity of preferably from about 1,000 to about 2,000,000 mPa·s at 25° C.

The viscosity can be measured by means of a glass capillary viscometer as set forth in Dow Corning Corporate Test Method CTM0004, Jul. 20, 1970. Suitable silicone fluids include polyalkyl siloxanes, polyaryl siloxanes, polyalkylaryl siloxanes, polyether siloxane copolymers, amino substituted silicones, quaternized silicones, and mixtures thereof. Other nonvolatile silicone compounds having conditioning properties can also be used.

In some embodiments, amino substituted silicones are preferably used. Preferred aminosilicones include, for example, those which conform to the general formula (I):

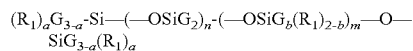

wherein G is hydrogen, phenyl, hydroxy, or $C_1$-$C_8$ alkyl, preferably methyl; a is 0 or an integer having a value from 1 to 3, preferably 1; b is 0, 1 or 2, preferably 1; n is a number from 0 to 1,999; m is an integer from 0 to 1,999; the sum of n and m is a number from 1 to 2,000; a and m are not both 0; $R_1$ is a monovalent radical conforming to the general formula $CqH_{2q}L$, wherein q is an integer having a value from 2 to 8 and L is selected from the following groups: —N($R_2$)$CH_2$—$CH_2$—N($R_2$)$_2$;  —N($R_2$)$_2$;  —N($R_2$)$_3$A$^-$; —N($R_2$)$CH_2$—$CH_2$—$NR_2H_2$A$^-$; wherein $R_2$ is hydrogen, phenyl, benzyl, or a saturated hydrocarbon radical, preferably an alkyl radical from about $C_1$ to about $C_{20}$; A$^-$ is a halide ion.

Highly preferred amino silicones are those corresponding to formula (I) wherein m=0, a=1, q=3, G=methyl, n is preferably from about 1500 to about 1700, more preferably about 1600; and L is —N(CH$_3$)$_2$ or —NH$_2$, more preferably —NH$_2$. Another highly preferred amino silicones are those corresponding to formula (I) wherein m=0, a=1, q=3, G=methyl, n is preferably from about 400 to about 600, more preferably about 500; and L is —N(CH$_3$)$_2$ or —NH$_2$, more preferably —NH$_2$. Such highly preferred amino silicones can be called as terminal aminosilicones, as one or both ends of the silicone chain are terminated by nitrogen containing group.

The above aminosilicones, when incorporated into the composition, can be mixed with solvent having a lower viscosity. Such solvents include, for example, polar or non-polar, volatile or non-volatile oils. Such oils include, for example, silicone oils, hydrocarbons, and esters. Among such a variety of solvents, preferred are those selected from the group consisting of non-polar, volatile hydrocarbons, volatile cyclic silicones, non-volatile linear silicones, and mixtures thereof. The non-volatile linear silicones useful herein are those having a viscosity of from about 1 to about 20,000 centistokes, preferably from about 20 to about 10,000 centistokes at 25° C. Among the preferred solvents, highly preferred are non-polar, volatile hydrocarbons, especially non-polar, volatile isoparaffins, in view of reducing the viscosity of the aminosilicones and providing improved hair conditioning benefits such as reduced friction on dry hair. Such mixtures have a viscosity of preferably from about 1,000 mPa·s to about 100,000 mPa·s, more preferably from about 5,000 mPa·s to about 50,000 mPa·s.

Other suitable alkylamino substituted silicone compounds include those having alkylamino substitutions as pendant groups of a silicone backbone. Highly preferred are those known as "amodimethicone". Commercially available amodimethicones useful herein include, for example, BY16-872 available from Dow Corning.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; coloring agents, such as any of the FD&C or D&C dyes; perfumes; ultraviolet and infrared screening and absorbing agents such as benzophenones; and antidandruff agents such as zinc pyrithione.

Product Forms

The compositions of the present invention can be in the form of rinse-off products or leave-on products, and can be formulated in a wide variety of product forms, including but not limited to creams, gels, emulsions, mousses and sprays. The composition of the present invention is especially suitable for hair conditioners especially rinse-off hair conditioners.

When used as a rinse-off conditioner, the composition is preferably used by the following steps:

(i) after shampooing hair, applying to the hair an effective amount of the conditioning composition for conditioning the hair; and (ii) then rinsing the hair.

Effective amount herein is, for example, from about 0.1 ml to about 2 ml per 10 g of hair, preferably from about 0.2 ml to about 1.5 ml per 10 g of hair.

Key Features of the Invention
A. The present invention is directed to a hair conditioning composition comprising:
  (a) a cationic surfactant;
  (b) a high melting point fatty compound having a melting point of 25° C. or higher;
  (c) a monoalkyl glyceryl ether; and
  (d) an aqueous carrier,
wherein the composition is used for providing volume benefits to hair.
B. The present invention is also directed to a hair conditioning composition comprising:
  (a) a cationic surfactant;
  (b) a high melting point fatty compound having a melting point of 25° C. or higher;
  (c) a monoalkyl glyceryl ether;
  (d) an aqueous carrier;
wherein the composition further comprises a polyol having at least 3 hydroxyl groups, and wherein the composition is a translucent hair conditioning composition having a transmittance of at least about 0.5%
C. The present invention is further directed to a hair conditioning composition comprising:
  (a) a cationic surfactant;
  (b) a high melting point fatty compound having a melting point of 25° C. or higher;
  (c) a monoalkyl glyceryl ether;
  (d) an aqueous carrier;
wherein the composition further comprises niacinamide.
D. The composition of any of the preceding features, wherein the monoalkyl portion of the monoalkyl glyceryl ether has from about 6 to about 30 carbons, preferably from about 12 to about 22 carbons.
The composition of any of the preceding features, wherein the monoalkyl portion of the monoalkyl glyceryl ether is a non-branched linear alkyl.
E. The composition of any of the preceding features, the composition is substantially free of polyglycerin.
F. The composition of the preceding feature B, wherein the composition has a transmittance of at least about 1.0%, preferably at least about 1.5%.
G. The composition of the preceding feature B, wherein the polyol is glycerin, sorbitol, and/or xylitol, preferably glycerin.
H. The composition of the preceding feature B, wherein the polyol is contained at a level of from about 40% to about 70%, preferably from about 45% to about 65%.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

TABLE 1

| Components | Compositions (wt %) | | | | | | | | |
| --- | --- | --- | --- | --- | --- | --- | --- | --- | --- |
| | Ex. 1 | Ex. 2 | Ex. 3 | Ex. 4 | Ex. 5 | CEx. i | CEx. ii | CEx. iii | CEx. iv |
| Batyl alcohol | 0.26 | 0.26 | 0.26 | 1.0 | 0.5 | — | — | 0.26 | 0.26 |
| Polyglycerin | — | — | — | — | — | — | — | 0.15 | 0.25 |
| Niacinamide | 0.5 | — | — | — | 2.0 | — | 0.5 | 0.5 | 0.5 |
| Stearamidopropyl dimethyl amine | 1.13 | 1.13 | — | 1.13 | 1.13 | 1.13 | 1.13 | 1.13 | 1.13 |
| L-glutamic acid | 0.37 | 0.37 | — | 0.37 | 0.37 | 0.37 | 0.37 | 0.37 | 0.37 |
| Behenyl trimethylammonium chloride | — | — | 2.85 | — | — | — | — | — | — |
| Cetyl alcohol | 1.17 | 1.17 | 1.01 | 1.17 | 1.17 | 1.17 | 1.17 | 1.17 | 1.17 |
| Stearyl alcohol | 2.0 | 2.0 | 2.53 | 2.0 | 2.0 | 2.0 | 2.0 | 2.0 | 2.0 |
| Glycerin | 50 | 50 | — | 50 | 50 | 50 | 50 | 50 | 50 |
| Silicone | — | — | 0.5 | — | — | — | — | — | — |
| Preservatives | 0.9 | 0.9 | 0.6 | 0.9 | 0.9 | 0.9 | 0.9 | 0.9 | 0.9 |
| Perfume | 0.4 | 0.4 | 0.4 | 0.4 | 0.4 | 0.4 | 0.4 | 0.4 | 0.4 |
| Deionized Water | q.s. to 100% | | | | | | | | |

Method of Preparation

The hair care compositions of "Ex. 1" through "Ex.5" of the present invention, and the hair care compositions of "CEx.i" and "CEx.iv" as comparative examples as shown above can be prepared by any conventional method well known in the art.

Properties and Conditioning Benefits

For some of the above compositions, properties and conditioning benefits are evaluated by the following methods. Results of the evaluation are also shown above.

The embodiments disclosed and represented by "Ex. 1" through "Ex. 5" are hair conditioning compositions of the present invention which are particularly useful for rinse-off use. Such embodiments have many advantages. For example, they provide styling and/or volume benefits while providing conditioning benefits. Ex. 1, 2, 4 and 5 also have translucent product appearances.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair conditioning composition comprising:
   (a) a cationic surfactant;
   (b) a high melting point fatty compound having a melting point of 25° C. or higher;
   (c) a batyl alcohol in an amount of from 0.1 wt. %; and
   (d) an aqueous carrier;
   wherein the hair conditioning composition further comprises niacinamide in an amount of from 0.2 wt. %;
   wherein the hair conditioning composition has a transmittance of at least about 1.0%;
   wherein the hair conditioning composition further comprises polyols at a level of above 30 wt. % selected from the group consisting of glycerin, sorbitol, and xylitol; and
   wherein the weight ratio between the cationic surfactant and the high melting point fatty acid compound is from 1:2 to 1:4.

2. The composition according to claim 1, wherein the composition is substantially free of polyglycerin.

3. The composition of claim 1, wherein the composition has a transmittance of at least about 1.5%.

4. The composition of claim 1, wherein the composition is substantially free of non-silicone nonionic thickening polymers selected from the group consisting of polysaccharide polymers, hydroxyethyl cellulose, hydroxypropyl cellulose, and combinations thereof.

* * * * *